United States Patent [19]

Haining

[11] Patent Number: 5,342,323
[45] Date of Patent: Aug. 30, 1994

[54] RETRACTABLE NEEDLE SYRINGE AND CAPPING SYSTEM

[76] Inventor: Michael L. Haining, 6731 Ashmore, Houston, Tex. 77069

[21] Appl. No.: 957,273

[22] Filed: Oct. 5, 1992

Related U.S. Application Data

[63] Continuation-in-part of Ser. No. 703,273, May 20, 1991, Pat. No. 5,152,750.

[51] Int. Cl.⁵ .............................................. A61M 5/00
[52] U.S. Cl. ................................. 604/195; 604/110
[58] Field of Search ............... 604/110, 195, 198, 218, 604/220, 222, 263

[56] References Cited

U.S. PATENT DOCUMENTS

| | | | |
|---|---|---|---|
| 4,026,287 | 5/1977 | Haller . | |
| 4,507,117 | 3/1985 | Vining | 604/196 |
| 4,643,200 | 2/1987 | Jennings, Jr. | 128/763 |
| 4,650,468 | 3/1987 | Jennings, Jr. | 604/110 |
| 4,675,005 | 6/1987 | DeLuccia | 604/110 |
| 4,692,156 | 9/1987 | Haller | 604/195 |
| 4,710,170 | 12/1987 | Haber et al. | 604/110 |
| 4,747,830 | 5/1988 | Gloyer et al. | 604/110 |
| 4,790,822 | 12/1988 | Haining | 604/110 |
| 4,950,251 | 8/1990 | Haining | 604/195 |
| 5,112,316 | 5/1992 | Venturini | 604/198 |
| 5,147,328 | 9/1992 | Dragosits et al. | 604/218 |
| 5,244,465 | 9/1993 | Michel | 604/218 |

FOREIGN PATENT DOCUMENTS 0327061 8/1989 European Pat. Off. .

*Primary Examiner*—C. Fred Rosenbaum
*Assistant Examiner*—Ronald Stright, Jr.
*Attorney, Agent, or Firm*—Richard L. Moseley

[57] ABSTRACT

A simplified retractable needle hypodermic syringe is provided which includes a barrel having a needle carrier mounted therein with a cannula attached thereto. A slidable plunger is mounted within the barrel which includes a shaft and hub for locking to the carrier. The plunger seal is conveniently mounted about the shaft between the plunger and the hub. A removable safety cap is provided to cover the upper end of the plunger and the barrel to prevent accidental depression of the plunger and engagement of the hub with the carrier before use. The cap is placed over the open end of the barrel after use to provide a closed container. The shaft is broken off at above the hub leaving the hub and carrier in the barrel.

6 Claims, 6 Drawing Sheets

1

RETRACTABLE NEEDLE SYRINGE AND CAPPING SYSTEM

This application is a continuation-in-part of my earlier patent application Ser. No. 07/703,273 filed May 20, 1991 now U.S. Pat. No. 5,152,750.

BACKGROUND OF THE INVENTION

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

Some of the recently patented retractable needle syringes include U.S. Pat. Nos. 4,692,156 (Haller); 4,675,005 (DeLuccia); 4,747,830 (Gloyer, et al); and my own patents 4,790,822 and 4,950,251. All of the syringes disclosed include a hypodermic needle mounted on a carrier which is slidable in the barrel. The plunger is locked to this carrier after the injection has been given and is withdrawn up into the barrel by withdrawal of the plunger. The simplest mechanism for locking the plunger to the carrier is disclosed as a projection on the lower end of the plunger which engages through an opening in the upper end of the carrier. Thus, the engagement requires a simple extra push on the plunger. There is the possibility that the plunger might become accidently engaged before use rendering the syringe useless. The present inventor has thus seen a need for a simple device to prevent depression of the plunger prior to use.

SUMMARY OF THE INVENTION

The retractable needle hypodermic syringe of the present invention is designed to include the minimum number of parts and to utilize as much as possible from currently available syringe parts. The syringe comprises a hollow cylindrical barrel open at both ends with a finger flange at the upper end and an inwardly projecting lip at the lower end. A rigid needle carrier of hard plastic is seated within the barrel on the lip with a projection extending out of the barrel for attachment of a standard hypodermic needle or cannula (the words are used interchangeably herein). A seal is provided in the form of an O ring which is seated between the end of the needle carrier and the lip. A plunger is slidably mounted within the barrel which defines the fluid chamber. A shaft extends from the lower end of the plunger which terminates in a hub. The hub is adapted to fit and lock into an enlarged bore near the upper end of the carrier. The plunger seal conveniently fits around the shaft between the end of the plunger and the hub. The hub clicks and locks into the carrier after use, allowing the carrier and needle to be retracted into the barrel. Additionally, the hub may be broken off in the carrier blocking the fluid channel and preventing any further use of the syringe.

A removable safety cap is provided which fits over the exposed end of the plunger and engages an extension of the barrel above the finger flanges. The safety cap conveniently fits over the open end of the syringe after the carrier and needle have been withdrawn into the barrel. The safety cap is secured over the open end by snap friction fit between the cap and the barrel.

DETAILED DESCRIPTION OF THE PREFERRED EMBODIMENT

For a detailed description of the preferred embodiment the reader is directed to the accompanying figures in which like components are given like numerals for ease of reference.

Figure 1:
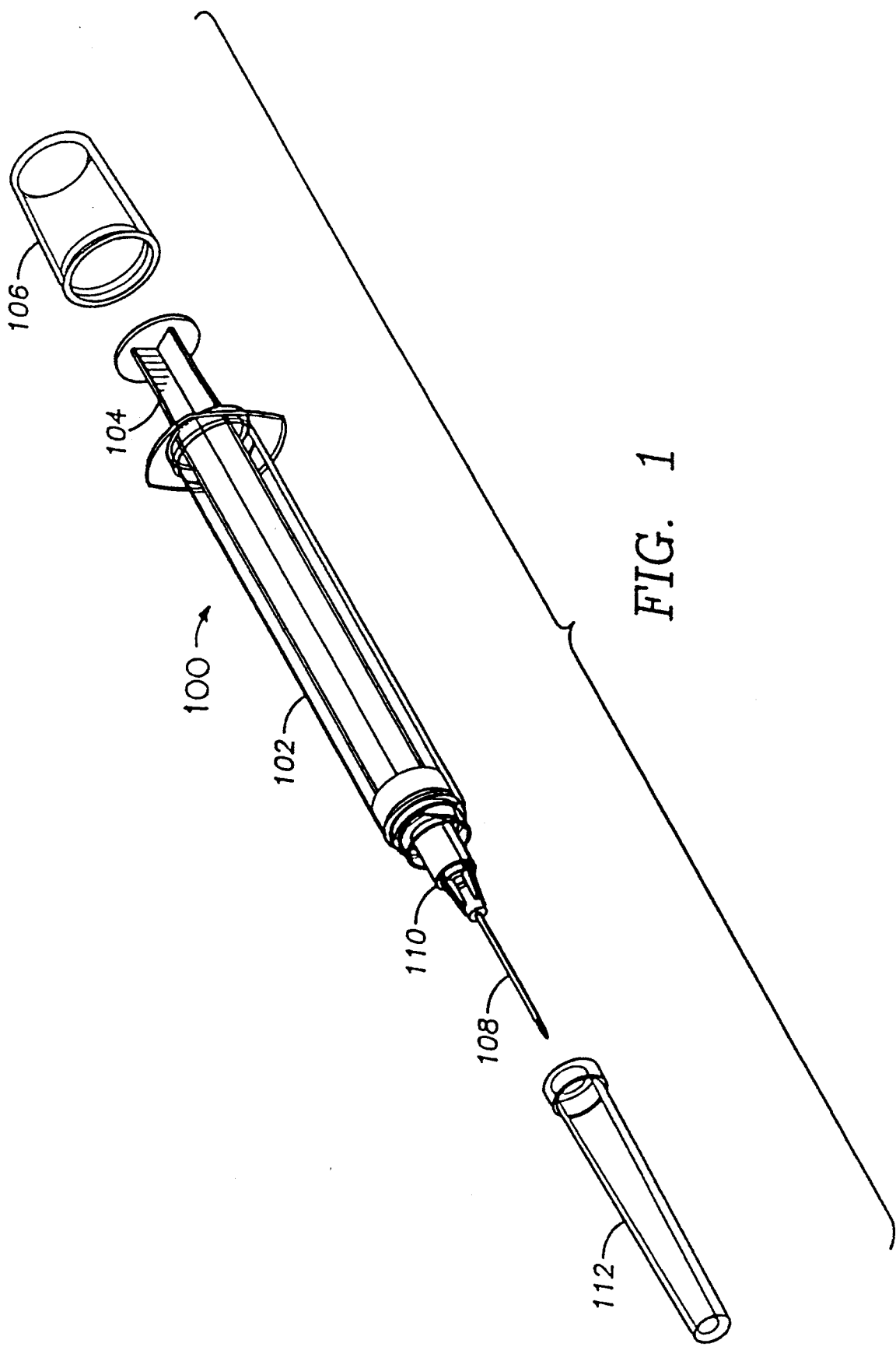
FIG. 1 is a perspective view of the retractable needle syringe of the present invention.
Figure 2:
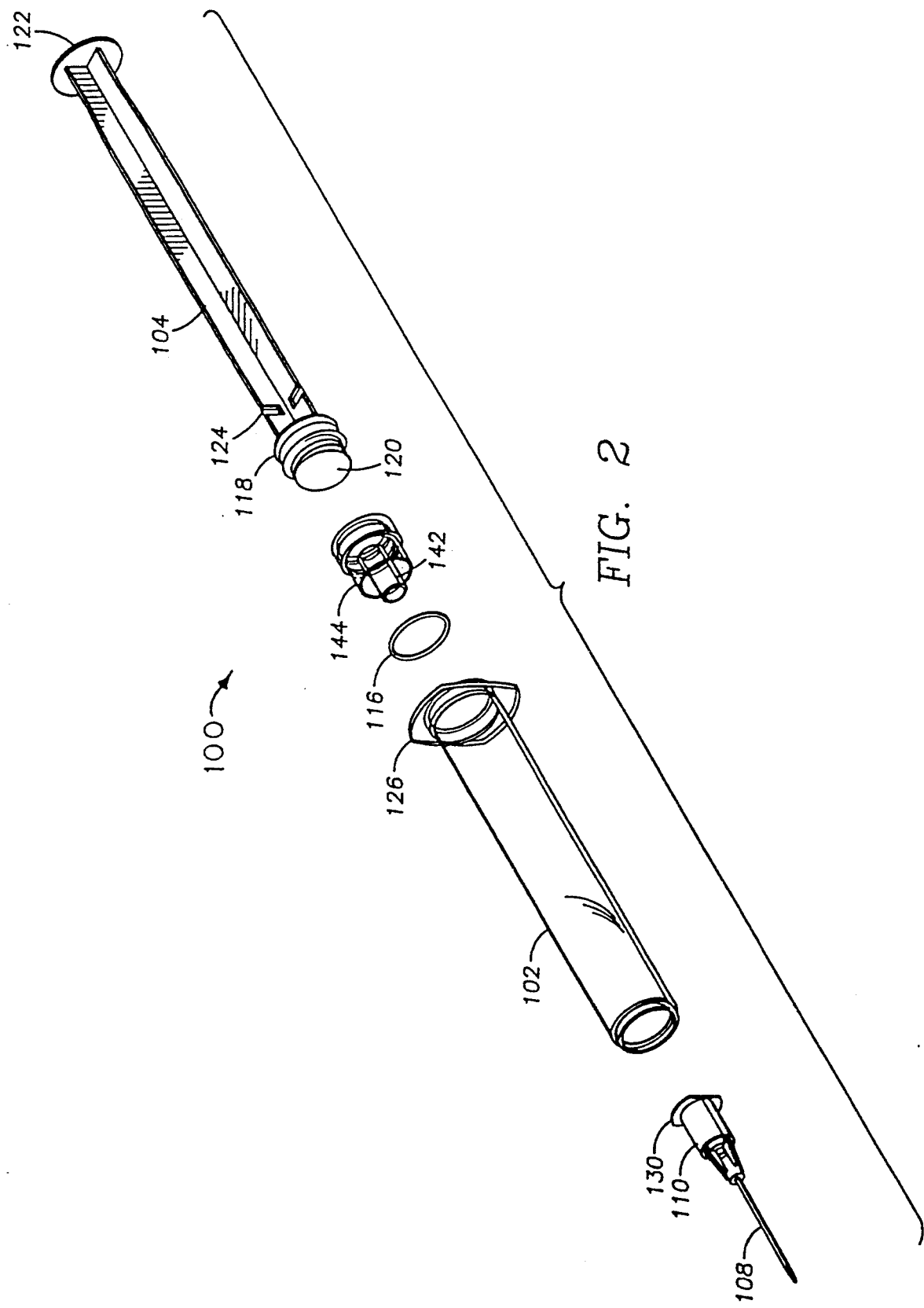
FIG. 2 is an exploded perspective view showing all of the parts of the retractable needle syringe of the present invention.

In FIGS. 1 and 2 the simplicity of the present retractable needle hypodermic syringe is illustrated. The syringe generally indicated at 100 is shown to comprise a hollow cylindrical barrel 102 of a semi-rigid deformable plastic with standard finger flanges 126 on one. A rigid needle carrier 114 of hard plastic is inserted into the barrel 102 through the flanged end opening and is seated on a lip 140 (shown in FIGS. 4 an 5) such that the extension 142 protrudes out of the barrel 102. A cannula 108 is attached to extension 142 by leuer lock 110 which engages internal threads in sleeve 144. The cannula is provided with protective sheath 112 for protection before use. Plunger 104 with a shaft about which is secured a rubber seal 118 is inserted into the barrel 102 and the syringe is ready for use. Plunger 104 includes upper surface 122 which is slightly larger in diameter than the barrel 102. An O ring 116 is seated between the needle carrier 114 and lip 140. The entire syringe thus consists of only seven distinct parts. Only the carrier, plunger and O ring are different from standard syringes once the needle mounting extension has been removed from the lower end of the barrel to provide lip 11. The cap 106 fits over an extension 146 (See FIGS. 3, and 5-7) of the barrel which protrudes beyond the finger flanges 126.

Figure 3:
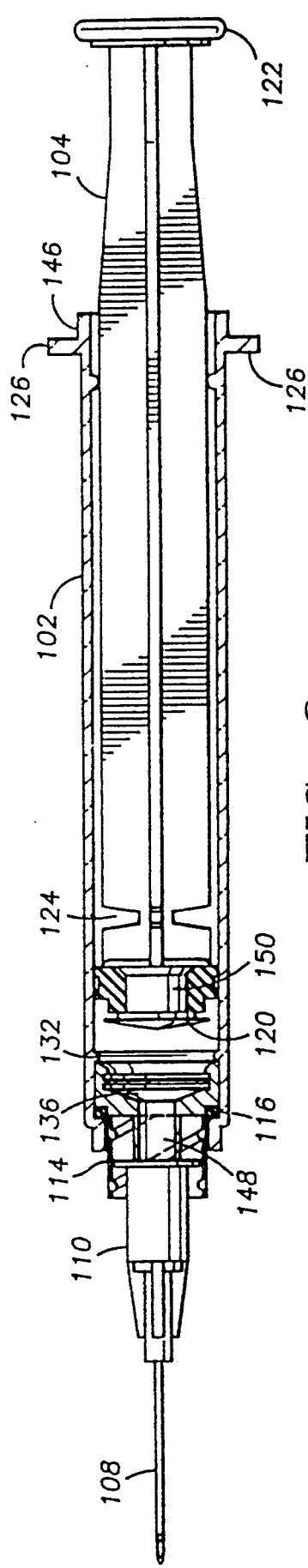
FIG. 3 is a side elevational view of the syringe of FIG. 1.
Figure 4:
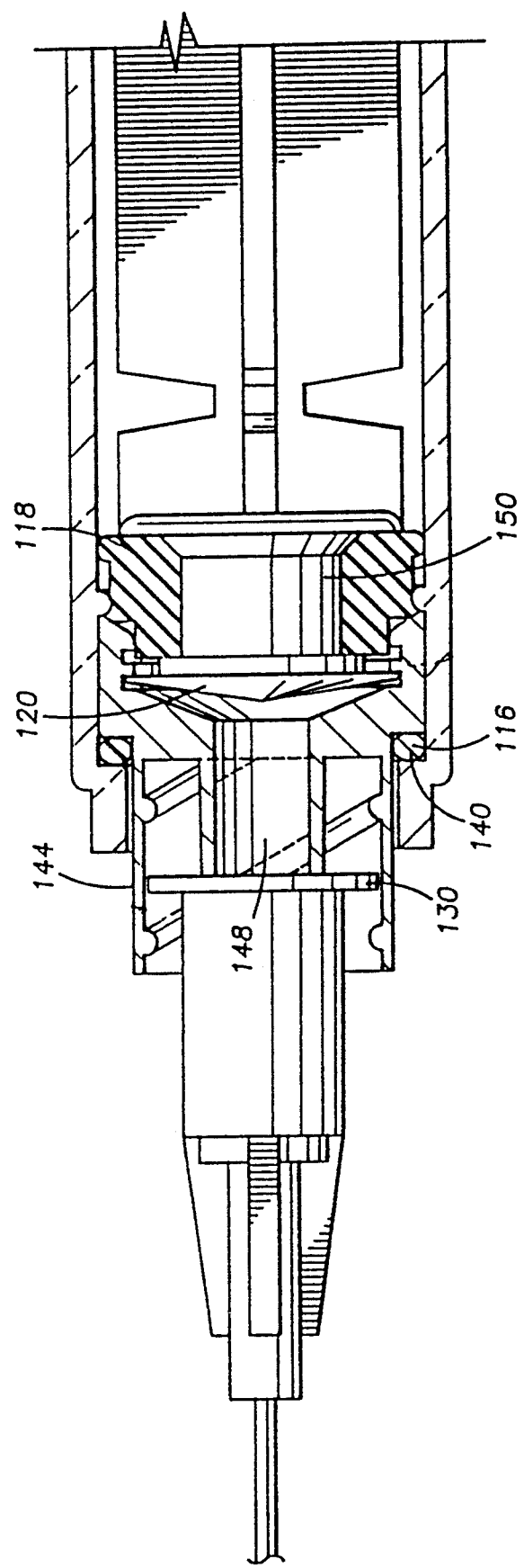
FIG. 4 is a side elevational view in partial cross section of the lower end of the assembled syringe of the present invention.

Referring now to FIGS. 3 and 4 details of the new parts are illustrated. The carrier 114 is shown seated on the lip 140 with extension 142 protruding out of the barrel. The outer diameter of the carrier is sized to provide a snug friction seal with the inner walls of the barrel 102. The O ring 116 is shown seated between the lip 140 and carrier 114. Additionally an internal ridge 132 within barrel 102 is located directly above the carrier 114 to aid in retaining the carrier in position while giving an injection. The leuer lock 110 of cannula 108 is secured to extension 142 by the engagement of flange 130 with internal threads in sleeve 144. A central bore 148 extends through the carrier 114 to provide fluid communication between the cannula 108 and barrel 102. Near the upper end of central bore 148 is an enlarged bore 136.

Plunger 104 is slidably mounted within barrel 102. Shaft 150 extends from the lower end of the plunger 104. At the lower end of shaft 150 is a hub 120 which is adapted to fit and lock into enlarged bore 136 in carrier 114.

Figure 6:
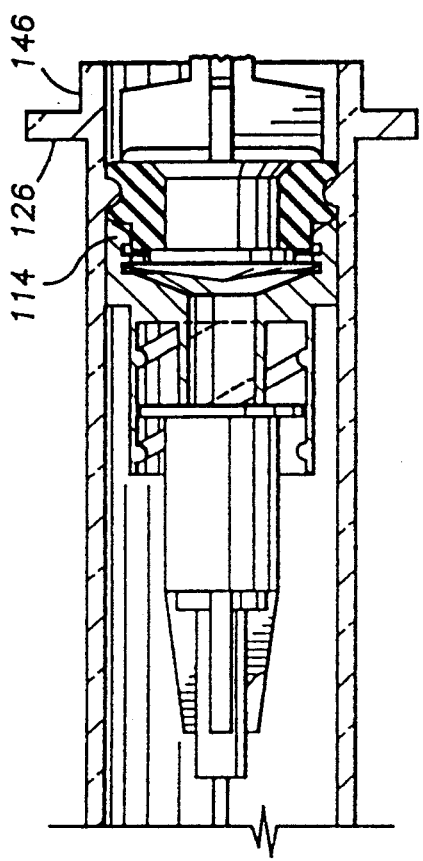
FIG. 6 is a side elevational view in partial cross section of the upper end of the assembled syringe with the needle retracted and hub broken.
Figure 5:
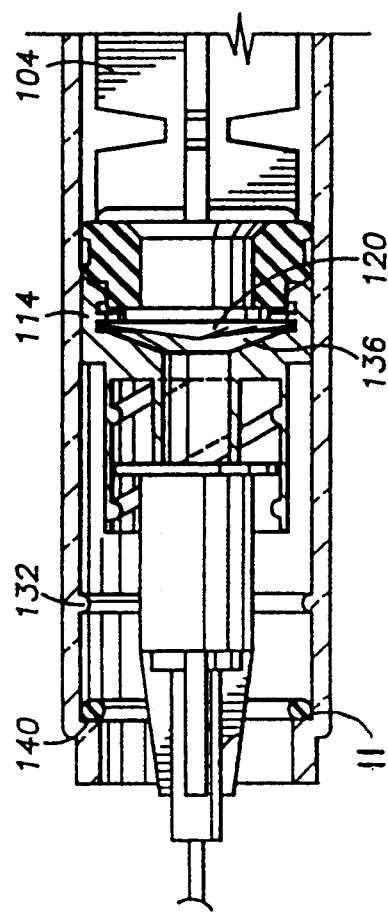
FIG. 5 is a side elevation view of the lower end of the syringe showing the needle being withdrawn into the barrel.
Figure 7:
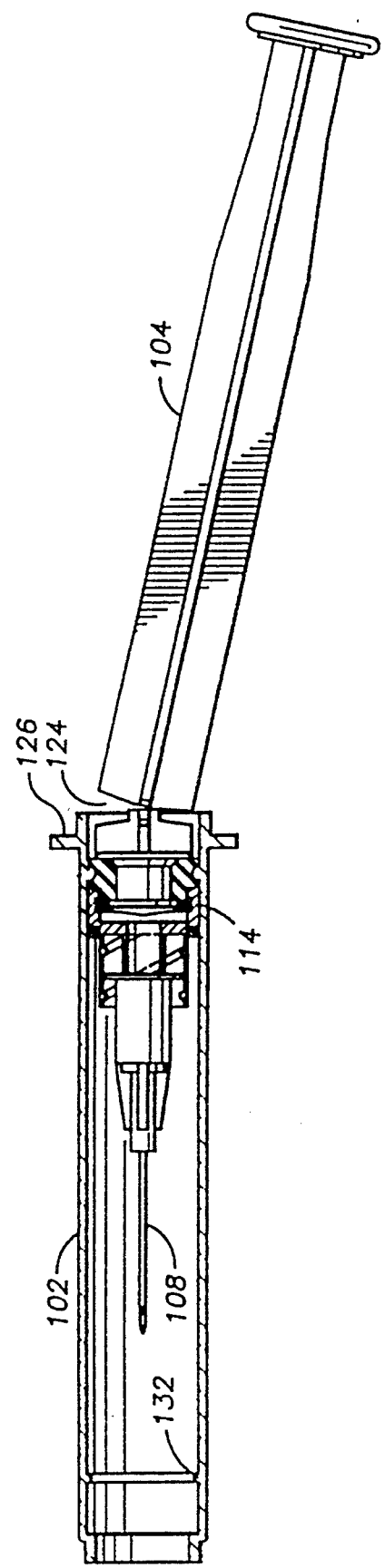
FIG. 7 is a side elevational view of the syringe of the present invention with the needle withdrawn into the barrel and the plunger broken off.

Referring now to FIGS. 5-7 the cannula 108 is shown retracted into the barrel 102. The hub 120 is shown engaged within enlarged bore 136. Notches 124 are provided in plunger 104 above the shaft to allow the plunger to be broken off leaving the lower end of the plunger with the hub engaged with the carrier in the barrel.

Figure 8:
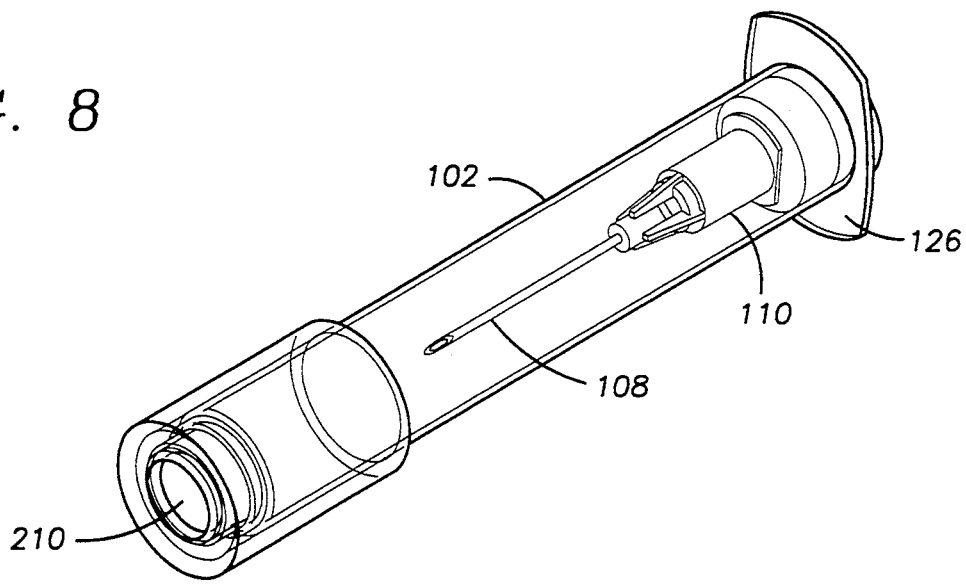
FIG. 8 is a perspective view of the syringe of the present invention with the needle withdrawn into the barrel and the safety cap placed over the open end.
Figure 9:
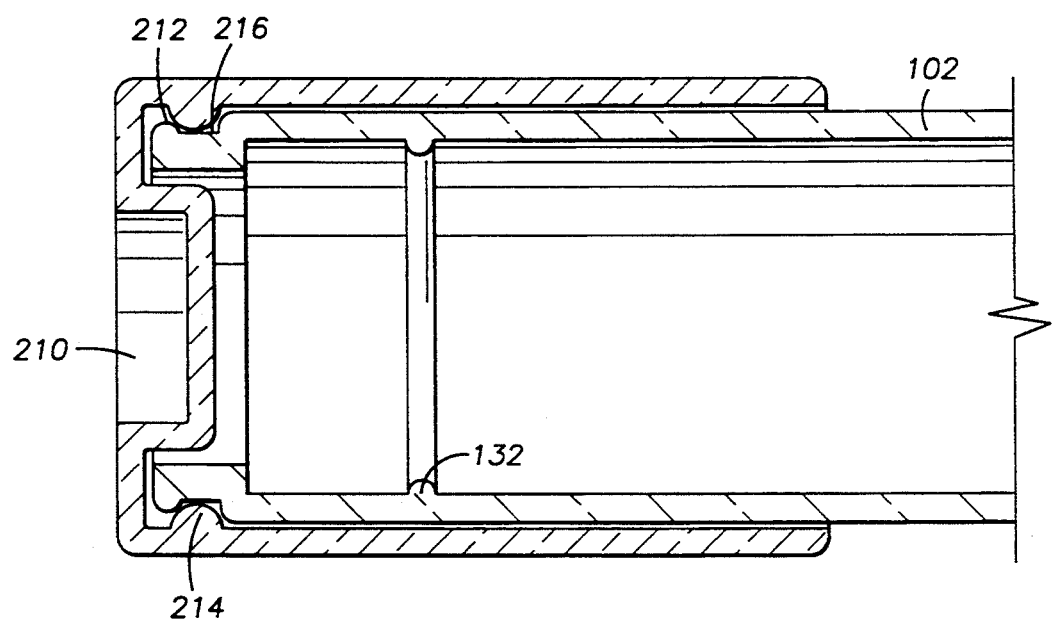
FIG. 9 is a side elevational view in cross section showing one embodiment of the cap locked onto the open lower end of the barrel.

Referring now to FIGS. 8 and 9 the new cap is illustrated. The cap 106 is shown to have a cylindrical indentation 210 in the end which protrudes down into the hollow portion of the cap. The indentation 210 creates an annular space 212 between the inner wall and the indentation which is substantially equal to the thickness of the barrel to provide a snug friction fit between the lower end of the barrel and the cap. This snug friction fit is considered to "lock" the cap around the lower end of the barrel and effectively seal the open end as shown in FIGS. 8 and 9. To ensure a lock an internally protruding ridge 214 is provided around the circumference within the cap which snaps into a small groove 216 on the outside of the lower end of the barrel.

Figure 10:
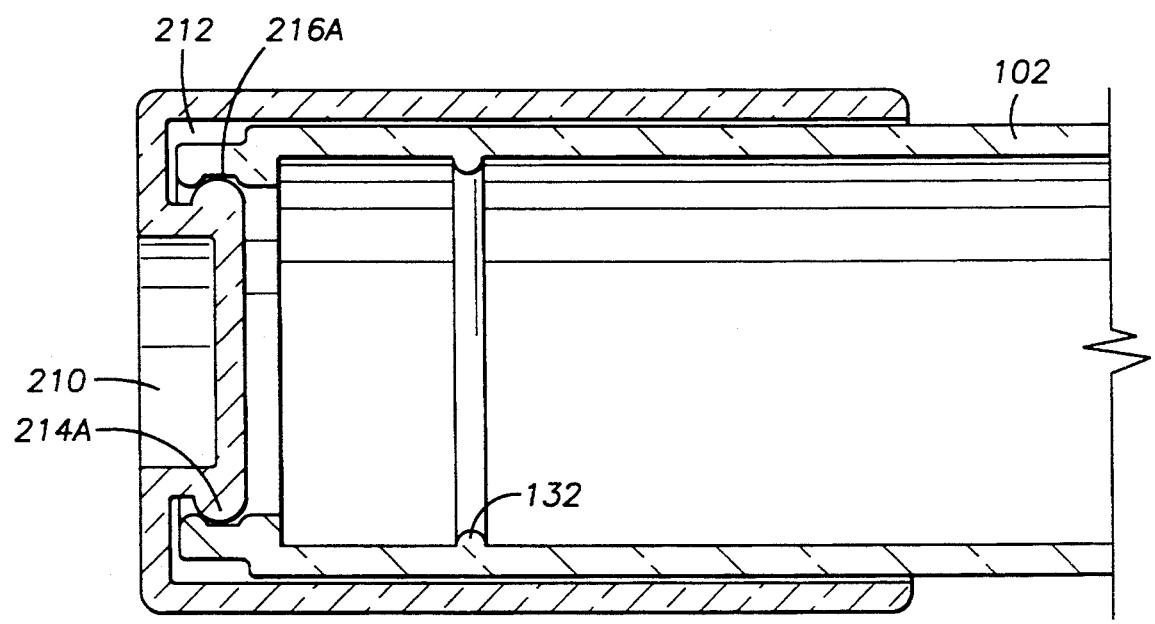
FIG. 10 is a side elevational view in cross section showing a second embodiment of the cap locked onto the open lower end of the barrel.

FIG. 10 illustrates a second embodiment of the locking mechanism of the cap which is a reversal of the first. The ridge 214A is external of the cylindrical indentation and the groove 216A is about the circumference of the lower end of the barrel.

In use the cap 106 is removed and the cannula 108 is inserted into the fluid to be injected and the fluid drawn into the chamber 102 by retraction of the plunger 104. Any air drawn in with the fluid may be removed in the usual manner—by inverting the syringe and thumping it until the bubble rises to the cannula end and depressing the plunger until fluid exits the cannula. The fluid may then be injected. As soon as the cannula is withdrawn from the recipient, the user may then further depress the plunger 104 until the hub 120 engages the carrier 114. After the hub 120 has engaged the carrier 114 the needle carrier with cannula 108 may then be retracted into the barrel 102. The plunger 104 may be broken off leaving shaft 150 and hub 120 blocking the internal passage to prevent any further use of the syringe. Finally, the cap 106 is placed over the now open end of the syringe barrel 102 to provide a neat closed package for disposal.

All of the materials of construction are conventional. For example, the barrel may be of transparent hard or soft plastic as is now commonly used in disposable syringes. The plunger and needle carrier are of hard plastic with the plunger seal and O ring being of standard rubber suitable for medical purposes.

What is claimed is:

1. A hypodermic syringe having a retractable needle, comprising:

a hollow cylindrical barrel open at both ends and having an inwardly projecting lip at the lower end and finger flanges at the upper end, said barrel having a ridge extending above said finger flanges;

a rigid cylindrical needle carrier mounted within said barrel and seated on said lip and retained in place by frictional sealing engagement between the outer diameter of said needle carrier and the inner wall of said barrel, said needle carrier having an extension protruding through the opening at the lower end of said barrel;

a hypodermic needle mounted on said extension;

a plunger slidably mounted in said barrel through the upper open end and defining a fluid chamber between said carrier and said plunger;

a central bore through said carrier and extension for fluid communication between said needle and said chamber;

an enlarged bore in said carrier near said chamber and coaxial with said central bore;

a shaft extending from the lower end of said plunger;

a hub on the lower end of said shaft adapted to lock into said enlarged bore; and a hollow cylindrical cap removably secured about said ridge above said finger flanges to prevent depression of said plunger prior to use, said cap having securing means to secure said cap about said lower end when said needle and carrier have been retracted into said barrel.

2. The hypodermic syringe of claim 1 further comprising a plunger seal member secured about said shaft between said plunger and said hub.

3. The hypodermic syringe of claim 1 further comprising an O ring seal mounted between said needle carrier and said lip.

4. The hypodermic syringe of claim 1 further comprising an internal ridge within said barrel directly above said needle carrier.

5. The hypodermic syringe of claim 1 wherein said cap includes a closed end and said securing means comprises an annular space near the closed end having an internally protruding ridge which engages a groove on the outer wall of said lower end of said barrel.

6. A hypodermic syringe having a retractable needle, comprising:

a hollow cylindrical barrel open at both ends and having an inwardly projecting lip at the lower end and finger flanges at the upper end, said barrel having a first extension above said finger flanges;

a rigid cylindrical needle carrier mounted within said barrel and seated on said lip and retained in place by frictional sealing engagement between the outer diameter of said needle carrier and the inner wall of said barrel, said needle carrier having a second extension protruding through the opening at the lower end of said barrel;

an inwardly extending circumferential ridge within said barrel directly above said carrier;

a hypodermic needle mounted on said extension;

a plunger slidably mounted in said barrel through the upper open end and defining a fluid chamber between said carrier and said plunger;

a central bore through said carrier and extension for fluid communication between said needle and said chamber;

an enlarged bore in said carrier near said chamber and coaxial with said central bore;

a shaft extending from the lower end of said plunger;

a hub on the lower end of said shaft adapted to lock into said enlarged bore;
a plunger seal member secured about said shaft between said plunger and said hub;
an O ring seal mounted between said needle carrier and said lip; and
a hollow cylindrical cap having a closed end removably secured about said first extension above said finger flanges to prevent depression of said plunger prior to use, said cap having an annular space at the closed end to secure said cap about said lower end after said carrier and needle have been retracted into said barrel.

* * * * *